(12) United States Patent
Carr et al.

(10) Patent No.: US 8,672,892 B2
(45) Date of Patent: Mar. 18, 2014

(54) TAMPER EVIDENT VACUUM TUBE HOLDER ASSEMBLY AND NEEDLE HUB ASSEMBLY THEREFOR

(75) Inventors: Ian Carr, Jaffrey, NH (US); Christian Schlerf, Keene, NH (US); William T. Torris, Greer, SC (US); Glynn Clements, Greenville, SC (US); Gregory J. Brown, Simpsonville, SC (US)

(73) Assignee: Smiths Medical ASD, Inc., Rockland, MA (US)

( * ) Notice: Subject to any disclaimer, the term of this patent is extended or adjusted under 35 U.S.C. 154(b) by 4058 days.

(21) Appl. No.: 10/827,434

(22) Filed: Apr. 20, 2004

(65) Prior Publication Data

US 2004/0254531 A1 Dec. 16, 2004

Related U.S. Application Data

(63) Continuation-in-part of application No. 10/419,934, filed on Apr. 22, 2003, now Pat. No. 8,172,808.

(51) Int. Cl.
*A61M 5/00* (2006.01)
(52) U.S. Cl.
USPC .......................................... 604/187; 604/192
(58) Field of Classification Search
USPC ......... 604/181, 187, 192–198, 110, 507, 263, 604/500
See application file for complete search history.

(56) References Cited

U.S. PATENT DOCUMENTS

| | | | | |
|---|---|---|---|---|
| 3,073,307 | A | * | 1/1963 | Stevens .......................... 604/192 |
| 4,900,309 | A | * | 2/1990 | Netherton et al. ............. 336/192 |
| 4,927,019 | A | | 5/1990 | Haber et al. |
| 5,277,311 | A | | 1/1994 | Hollister |
| 5,823,997 | A | | 10/1998 | Thorne |
| 5,980,488 | A | | 11/1999 | Thorne |
| 6,027,482 | A | | 2/2000 | Imbert |
| 6,436,086 | B1 | * | 8/2002 | Newby et al. .................. 604/507 |
| 2003/0028152 | A1 | | 2/2003 | Alesi et al. |

OTHER PUBLICATIONS

Monoject Magellan Safety Blood Collection Needle (flyer) Tyco Healthcare Sep. 2003.

* cited by examiner

*Primary Examiner* — Kevin C Sirmons
*Assistant Examiner* — Phillip Gray
(74) *Attorney, Agent, or Firm* — Louis Woo

(57) ABSTRACT

A one piece molded vacuum tube holder is fitted with a one piece molded needle hub assembly. A needle protection device is further rotatably mounted to the neck of the one piece vacuum tube holder. One portion of a locking mechanism is provided at the neck of the one piece vacuum tube holder and a second portion of the locking mechanism is provided at the needle hub of the needle hub assembly, so that when the needle hub assembly is press fit to the vacuum tube holder, the two portions of the locking mechanism will coact to fixedly retain the needle hub assembly within the vacuum tube holder. The one piece vacuum tube holder is configured to have an elongate needle cover integrally extending from its neck. A finger grasp mechanism may be coupled to the needle cover.

6 Claims, 10 Drawing Sheets

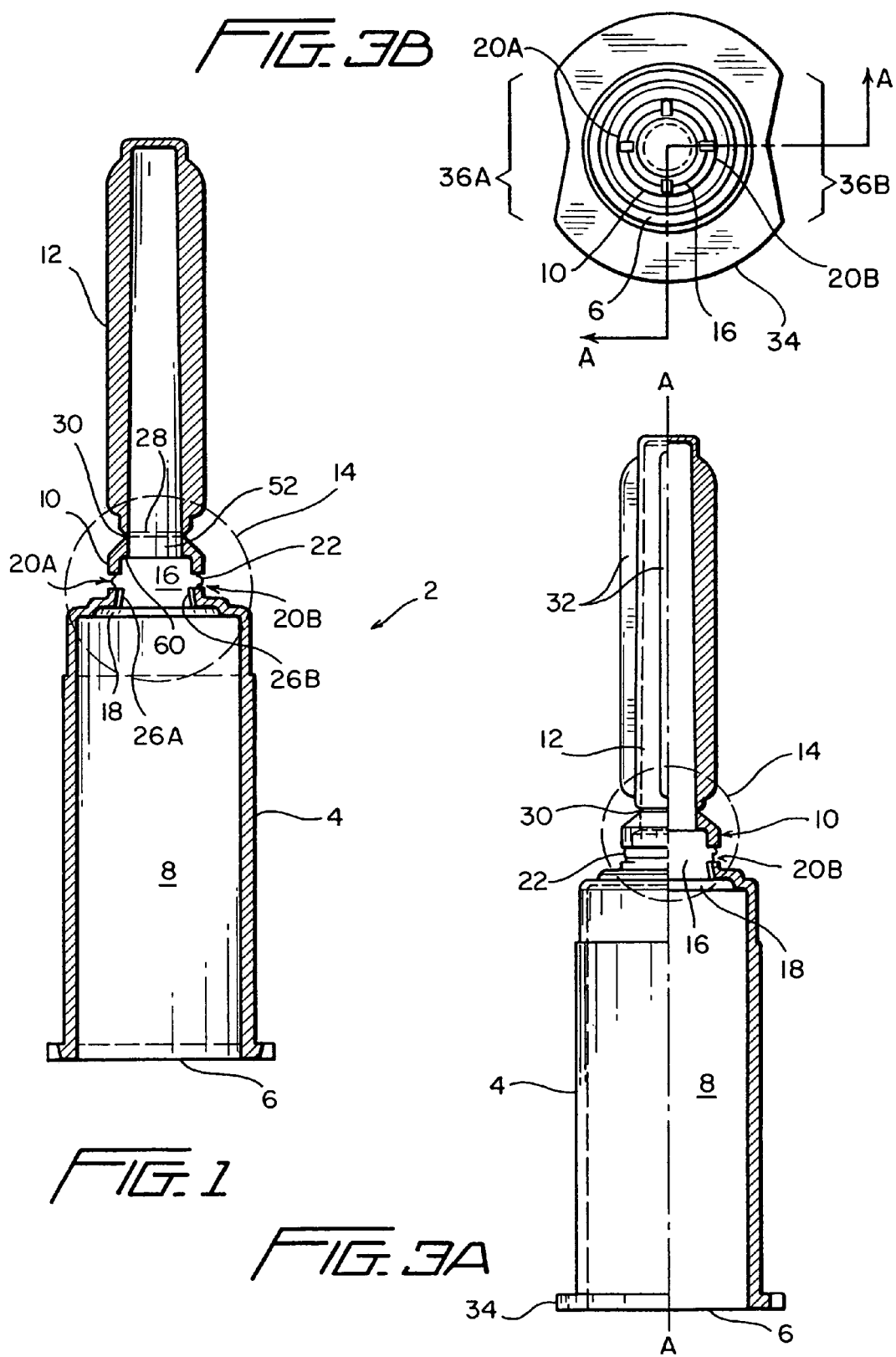

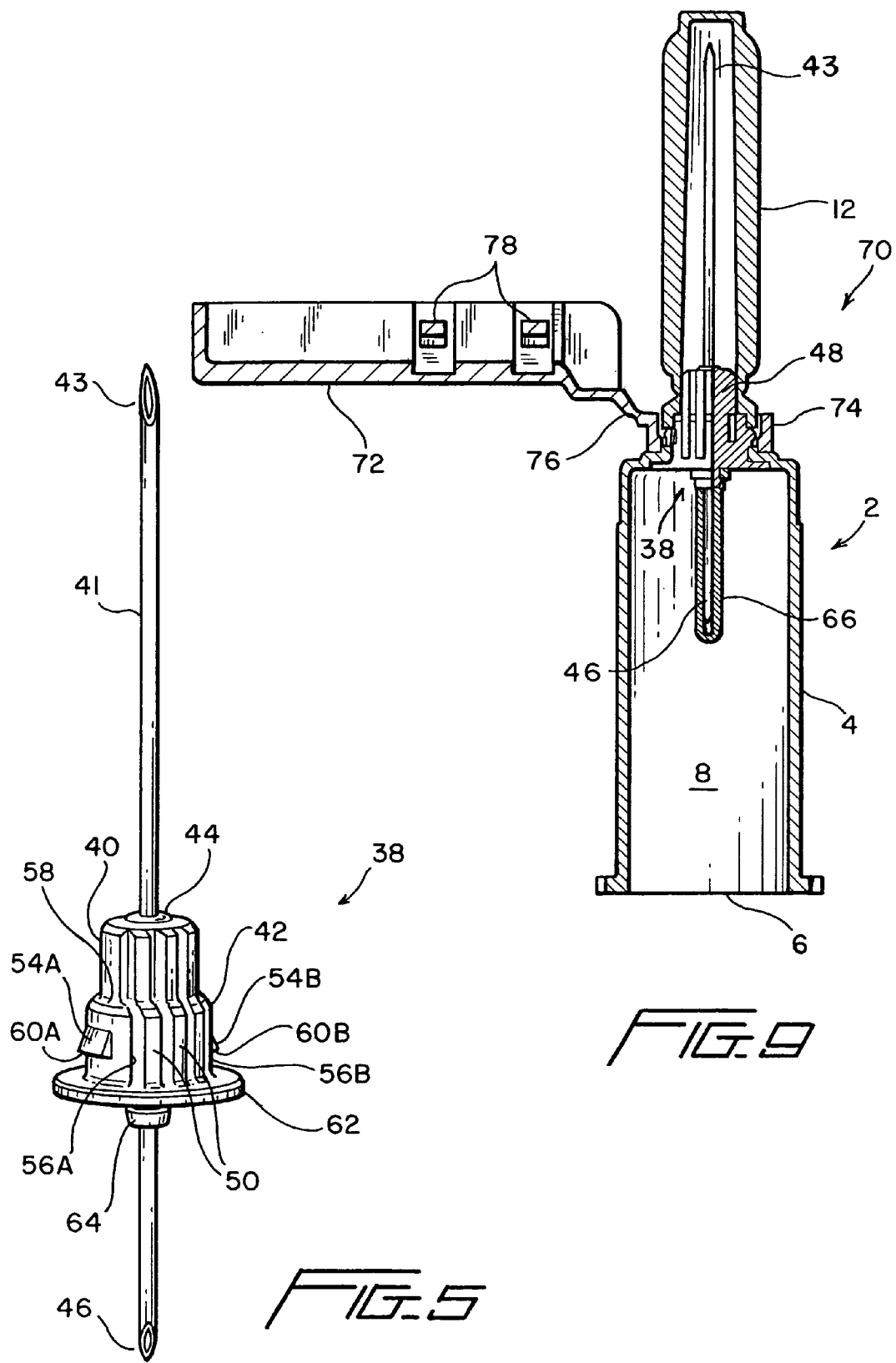

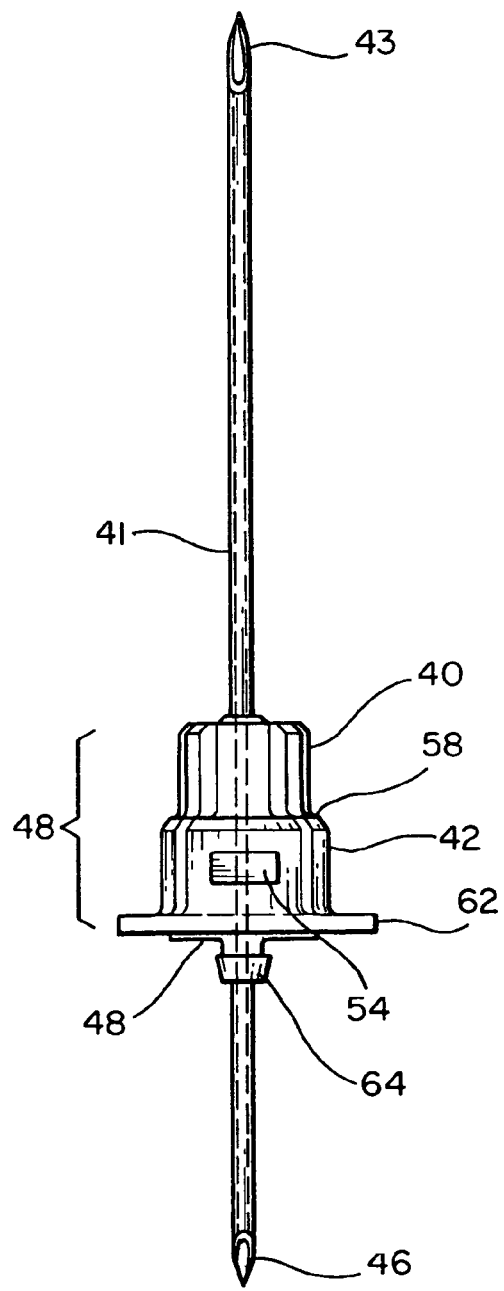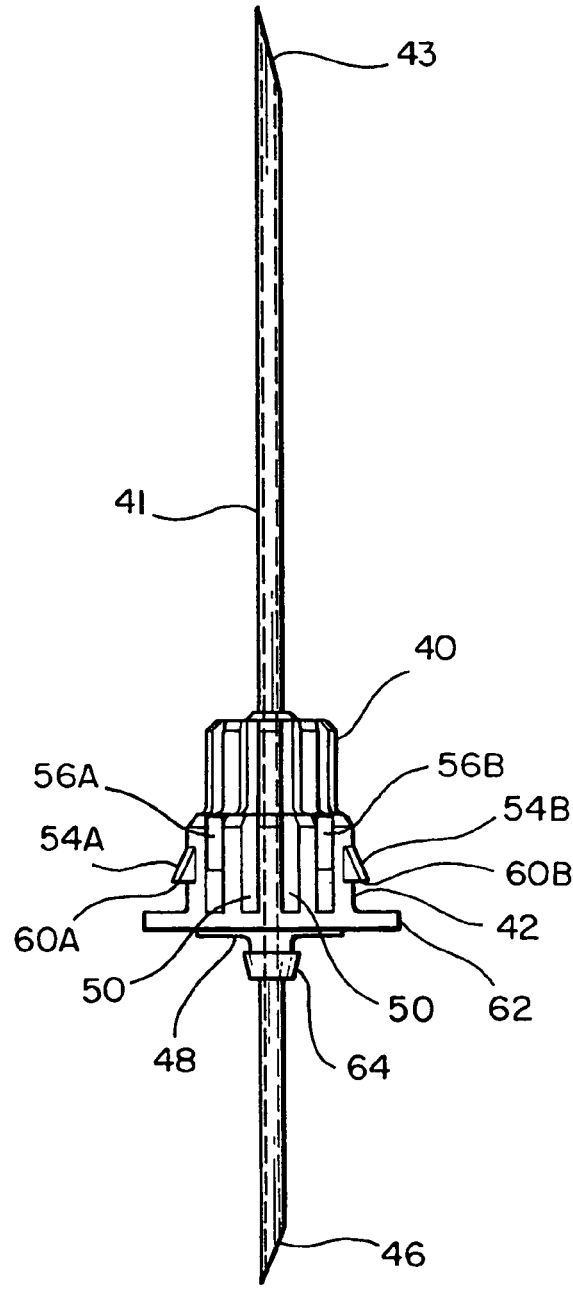

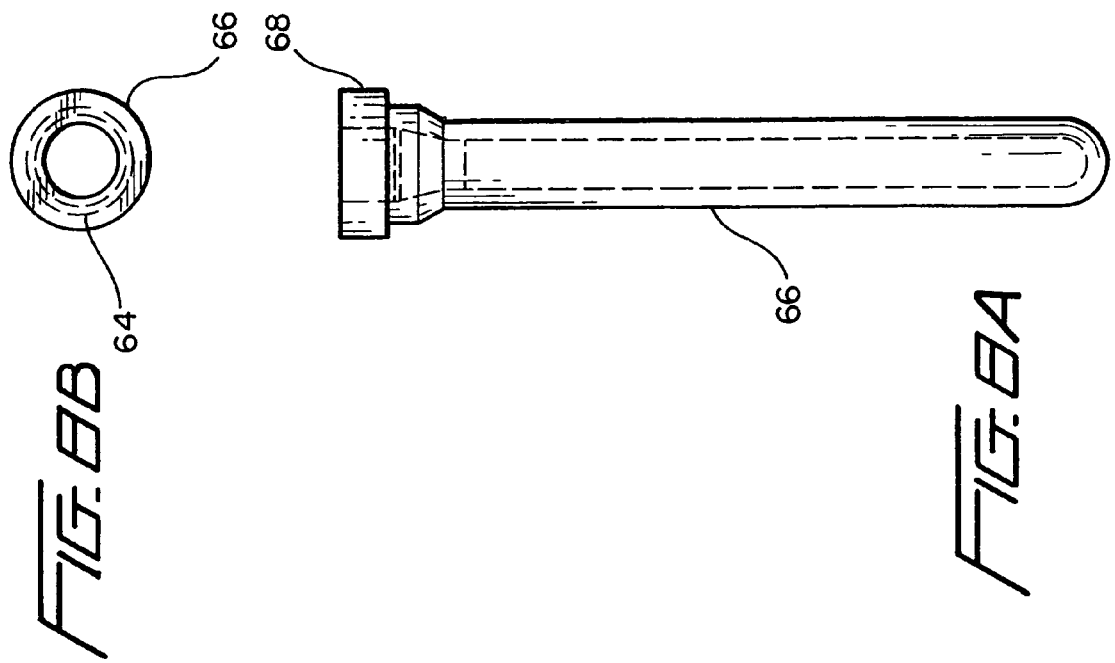
FIG.8B
FIG.8A
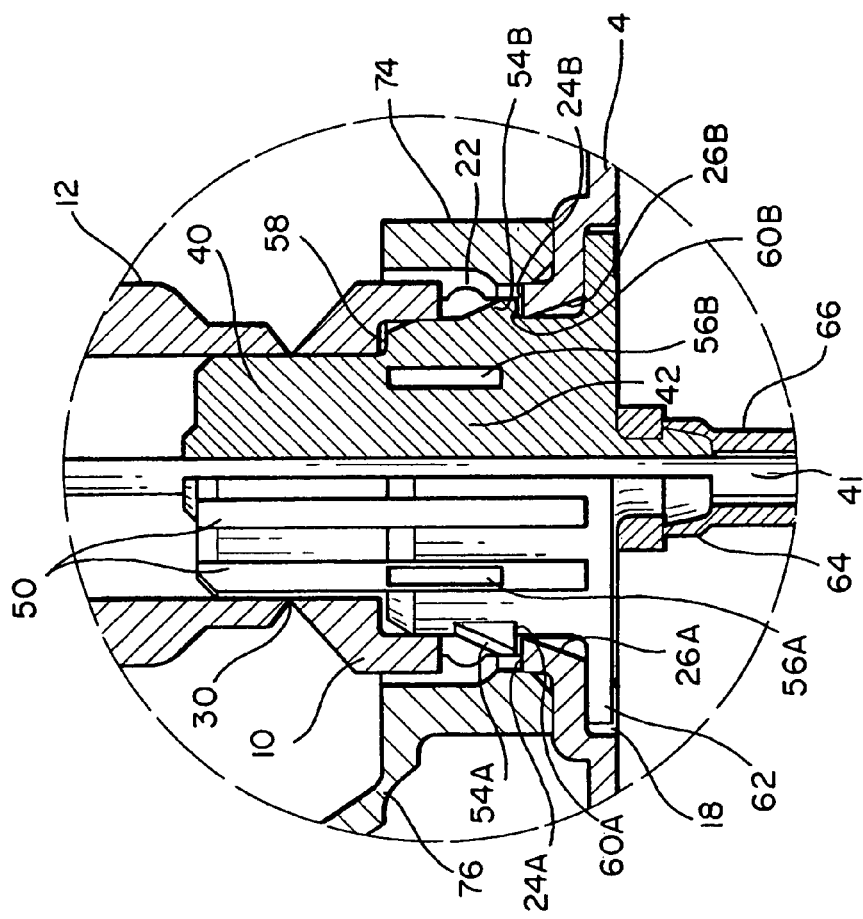
FIG.10

A-A

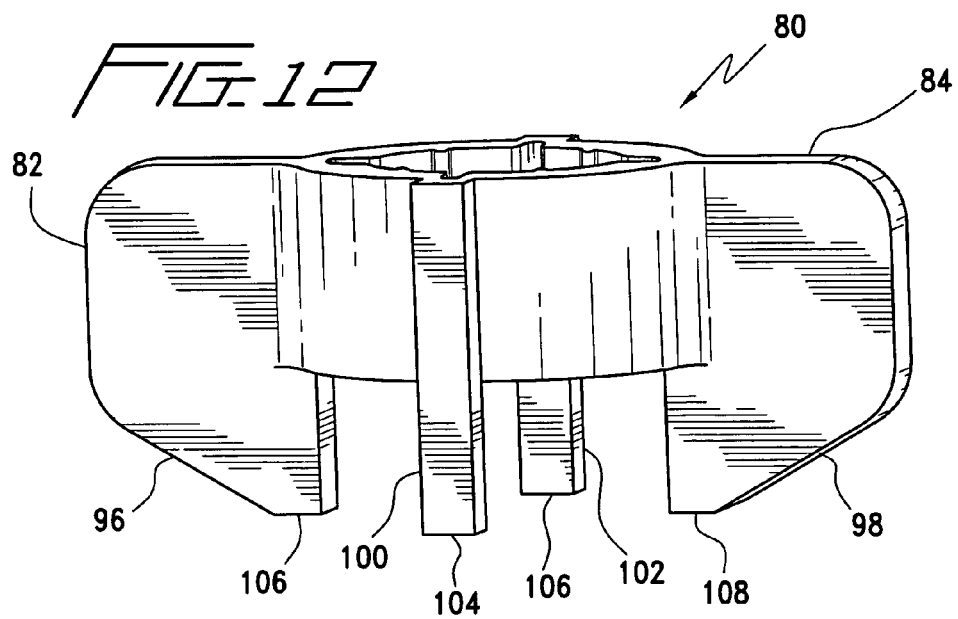
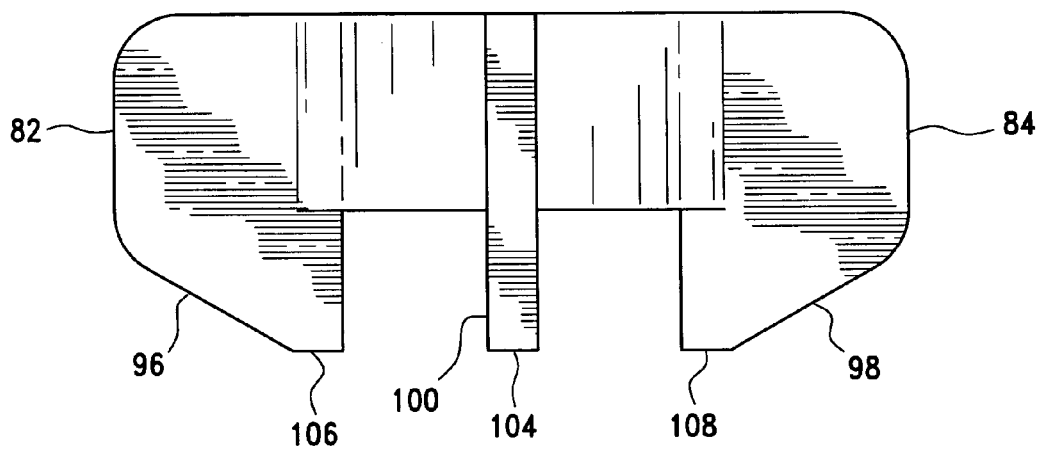
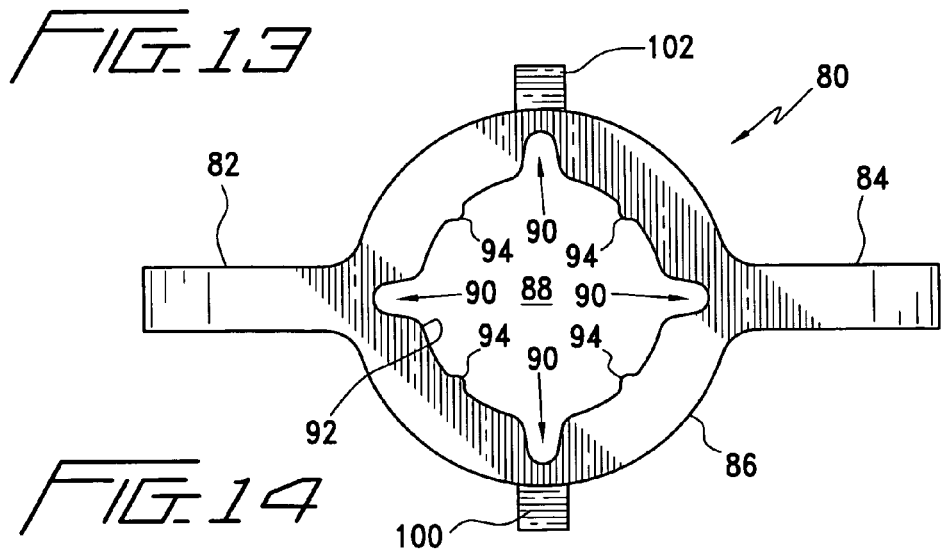

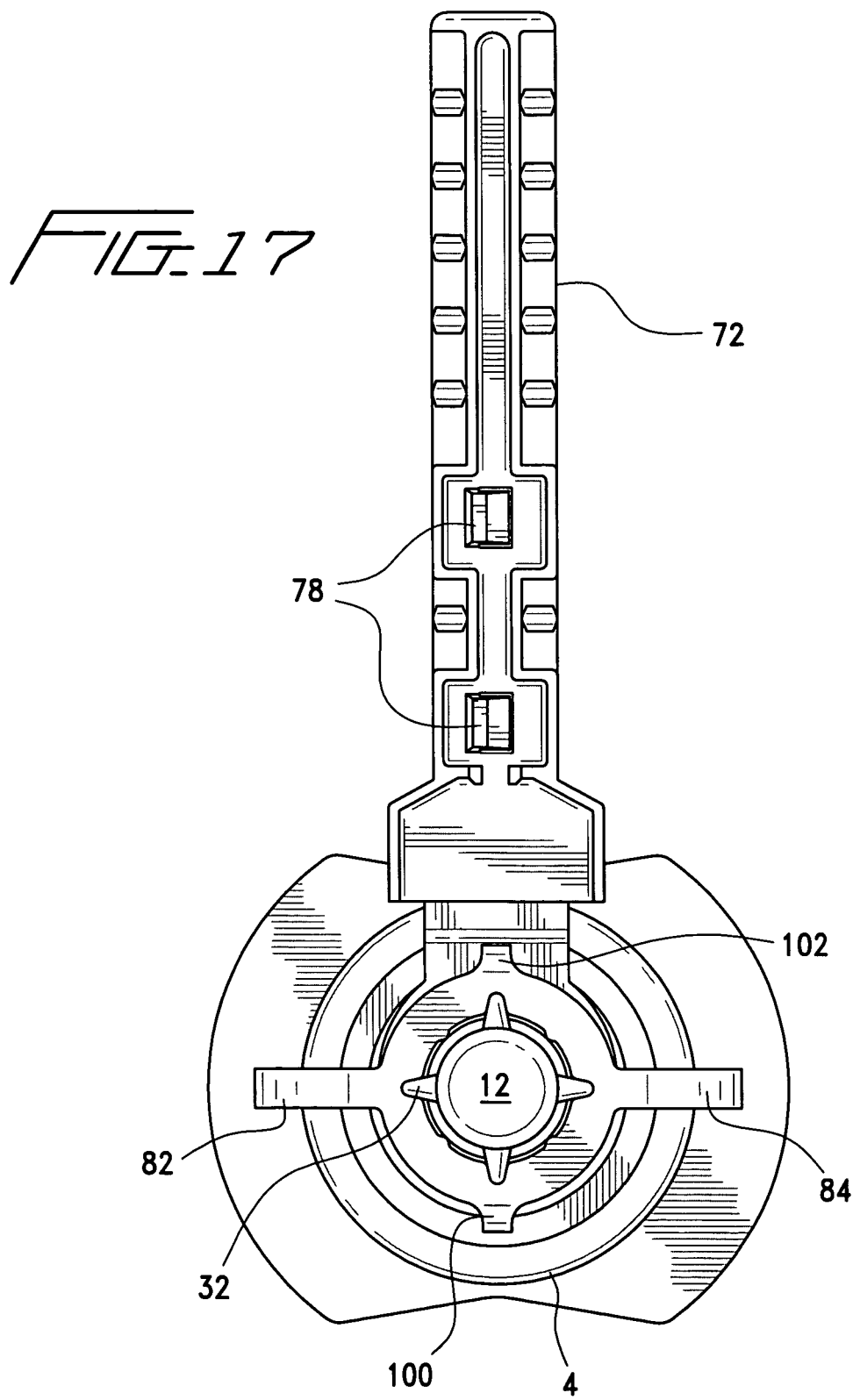

TAMPER EVIDENT VACUUM TUBE HOLDER ASSEMBLY AND NEEDLE HUB ASSEMBLY THEREFOR

This application is a continuation-in-part of application Ser. No. 10/419,934 filed Apr. 22, 2003 now U.S. Pat. No. 8,172,808.

FIELD OF THE INVENTION

The following invention relates to a device for holding a fluid container tube such as a vacuum tube, and particularly relates to a vacuum tube holder assembly that is readily manufactured, provides a built in tamper evident seal and has a needle protection housing that securely covers a contaminated needle after use.

BACKGROUND OF THE INVENTION

In U.S. Pat. No. 5,139,489 a vacuum tube holder has attached thereto a protective needle housing which is pivotable to cover an exposed needle of a double-ended needle assembly threaded to the vacuum tube holder. In U.S. Pat. No. 5,154,285, a needle protection housing is mounted to the neck of the vacuum tube holder by means of a collar, so that the housing is rotatable with respect to the neck of the vacuum tube holder. For both of the devices disclosed in the '489 and '285 patents, prior to use and shipping, the double-ended needle is capped at both ends.

Conventionally, a double-ended needle is shipped in a container that covers both ends of the needle. The container is taped with a piece of paper, or other sealing material, to provide evidence that it has not been tampered with prior to use. There has not been any tampering if there is no tear on the paper seal when a phlebotomist takes the double-ended needle out of the container and threads it to the vacuum tube holder or Vacutainer holder. Thus, to use the devices disclosed in the '489 and '285 patents, a user has to first remove the double-ended needle from its container and then thread the double-ended needle to the vacuum tube holder. Moreover, the user has to carry both the double-ended needle and the vacuum tube holder as separate units. The disclosures of the '489 and '285 patents are incorporated by reference herein.

SUMMARY OF THE PRESENT INVENTION

The present invention vacuum tube holder assembly is shipped as a single piece, with the various components pre-assembled. The vacuum tube holder is a molded one piece component that includes an elongate needle cover that integrally extends from the neck of the body of the vacuum tube holder. At the junction where the elongate needle cover meets the neck of the holder, there is a thinning out of material such as for example by a circumferential notching thereat. When a predetermined torque force is applied to the needle cover relative to either the neck or the body of the vacuum tube holder, the needle cover is readily removed or separated by the twisting motion. Once removed, the needle cover could not be reattached to the neck of the vacuum tube holder. Accordingly, a built in tamper evident seal is provided for the vacuum tube holder of the instant invention, in that a user knows that the vacuum tube holder has been tampered with if the needle cover is missing or is hanging loosely from the neck of the body of the vacuum tube holder.

A needle hub assembly specifically manufactured to be a component of the vacuum tube holder assembly is press fit through the opening of the vacuum tube holder body towards the neck of the vacuum tube holder. The needle hub of the needle hub assembly has a dimension that allows it to mate to the aperture of the neck of the vacuum tube holder which is smaller than the opening of the vacuum tube holder. At the needle hub of the needle hub assembly there are formed two catches that are movable transversely to the needle hub when biased. To enable the transverse movements for the catches, respective through slots are formed in the needle hub behind each of the catches. As the needle hub is press fit to the neck of the vacuum tube container, the catches would first compress, since they are in contact with upward sloping ramps at the inside wall of the neck, in order to pass the aperture of the neck. When the needle hub is pushed sufficiently far into the neck of the vacuum tube holder, openings or orifices formed on the opposite sides of the neck enable the catches, upon mating with those orifices, to return to their original shapes as they latch onto the orifices. Once the catches latch onto their respective orifices at the neck of the vacuum tube holder, the needle hub assembly is fixedly retained within the vacuum tube holder.

There is a raised boss or protuberance circumferentially formed at the outer surface of the neck of the vacuum tube holder. Rotatably mounted to the protuberance is a collar having an internal groove that mates to the protuberance. The tolerances provided for the internal groove of the collar and the protuberance about the neck of the vacuum tube holder during the molding process are such that the friction between the internal groove of the collar and the protuberance would hold the collar in place so long as an external torque force is not applied thereagainst. The collar is therefore not freely rotatable about the neck of the vacuum tube holder. Hingedly connected to the collar is a needle protection housing. Integral hooks are provided in the housing.

The vacuum tube holder assembly therefore includes the vacuum tube holder, the needle hub assembly fitted into the holder and the needle protection housing rotatably mounted to the neck of the vacuum tube holder. The opening at the end of the vacuum tube holder to which a vacuum tube or fluid container is insertable during use may be covered by a seal so that the vacuum tube holder assembly may be readily sterilized and shipped without any need for additional packaging.

To assist in the removal of the needle cover from the body of the vacuum tube holder, a finger grasp ring in the form of a wing nut is coupled to the needle cover, at a desired location therealong, for example at the proximal portion thereof. The wing nut, as its name implies, may have a number of wings extending from its outer wall so as to enable a user to readily grasp the wings of the wing nut with her fingers and apply a torque to the wing nut to remove the needle cover from the neck of the body. By providing the wing nut to the needle cover, the circumferential notching at the junction where the needle cover meets the neck of the holder could be thickened to thereby prevent any inadvertent breaking off of the needle cover from the neck during shipping or handling. The predetermined torque for separating the thickened notched junction has been determined to be greater than approximately 60 ounce inches. But by grasping and twisting the wing nut, a user only needs to exert a torque force substantially similar to, or not greatly exceeding, that used for the non-wingnut embodiment vacuum tube holder assembly, in order to break the thickened notched junction.

BRIEF DESCRIPTION OF THE DRAWINGS

The present invention will become more apparent and the invention itself will be best understood by reference to the following description of the present invention taken in conjunction with the accompanying drawings wherein:

FIG. 1 is a cross-sectional view of the one-piece molded vacuum tube holder of the instant invention;

FIG. 3a is a semi-cross-sectional view of the FIG. 1 vacuum tube holder;

FIG. 3b is a bottom view looking into the cavity of the body of the vacuum tube holder of FIG. 3a;

FIG. 4 is an enlarged view of the semi-cross-sectional view of the neck of the vacuum tube holder shown in FIG. 3a;

FIG. 5 is a perspective view of a needle hub assembly of the instant invention;

FIG. 6 is a side view of the needle hub assembly;

FIG. 7 is another side view of the needle hub assembly;

FIG. 8a is a side view of a rubber boot to be fitted to the end of a double-ended needle that extends into the vacuum tube holder of FIG. 1;

FIG. 8b is a top view of the rubber boot shown in FIG. 8a;

FIG. 9 is a cross-sectional view of the vacuum tube holder assembly of the instant invention;

FIG. 10 is an enlarged semi-cross-sectional view of the neck area of the inventive vacuum tube holder assembly;

FIG. 12 is perspective view of a second embodiment of the wing nut to be added to the inventive vacuum tube holder assembly;

FIG. 13 is a side view of the FIG. 12 wing nut;

FIG. 14 is a top view of the FIG. 12 wing nut;

FIG. 17 is a top view of the FIG. 15 vacuum tube holder assembly.

DETAILED DESCRIPTION OF THE INVENTION

Figure 4:
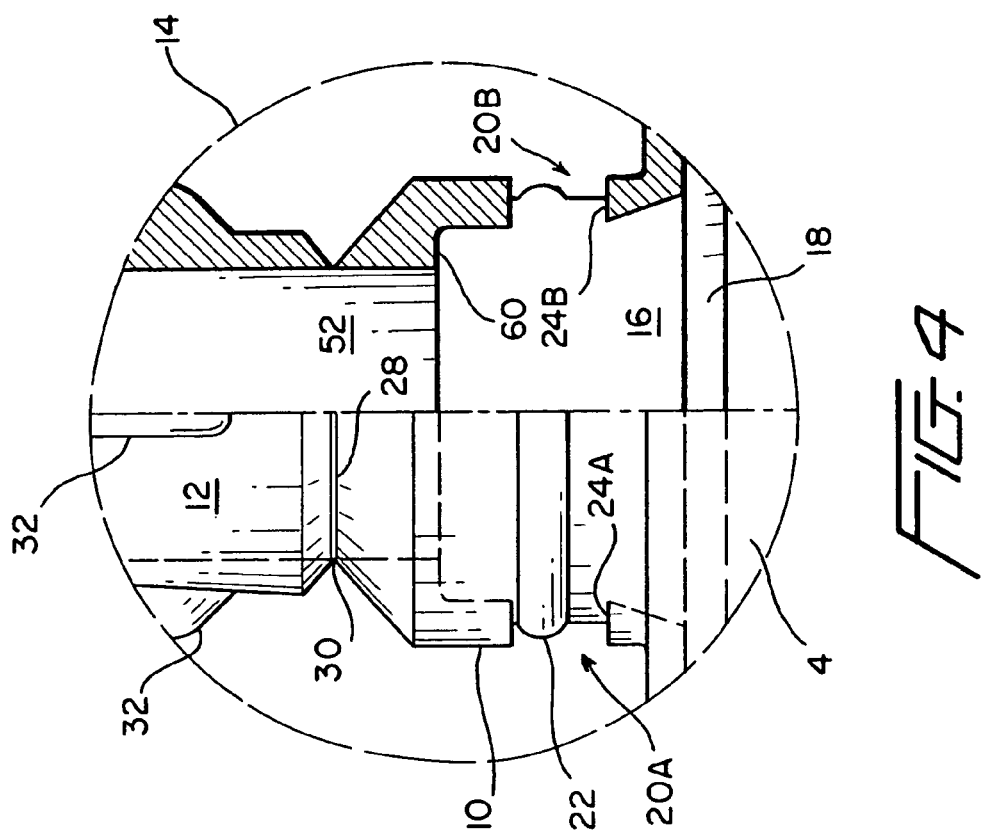

With reference to FIG. 1, a one piece molded vacuum tube holder 2, as shown in cross section, includes a cylindrical body 4 having an opening 6 at its one end dimensioned to receive a conventional fluid storage vacuum tube into the cavity 8 of cylindrical body 4. A neck portion 10 extends integrally from body 4. Extending integrally from neck 10 is an elongate needle cover 12. The one piece vacuum tube holder may be formed by molding and may be made from polypropylene.

Figure 2:
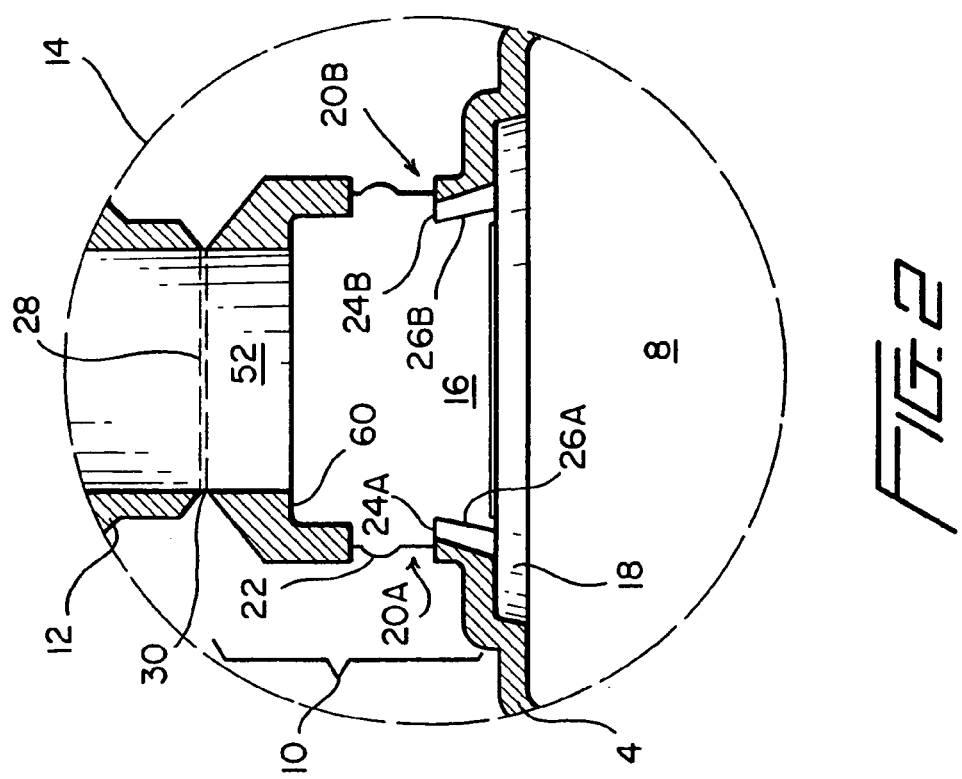
FIG. 2 is an enlarged cross-sectional view of the neck of the vacuum tube holder of FIG. 1.

An exploded view of FIG. 1, designated 14, is shown in FIG. 2.

With reference to both FIGS. 1 and 2, note that neck 10 of the vacuum tube holder 2 has an opening or aperture 16 at its proximal end merging into cavity 8 of body 4. Aperture 16 is dimensioned to accept a needle hub such as that shown in FIG. 5, to be discussed more fully later. At the junction where neck 10 meets with body 4, there is an internal recess 18 to which the base of the needle hub may rest. There are two openings or orifices 20a and 20b formed at the opposite sides, or 180°, at the wall of neck 10. Circumferentially formed about the outer wall surface of neck 10, possibly interrupted by orifices 20a and 20b, is a raised boss or protuberance 22 to which, as will be discussed later, a collar to which a needle protection housing is hingedly connected, as shown in FIG. 9, is rotatably coupled.

As best shown in FIG. 2, the respective lower portions of orifices 20a and 20b are formed by lower supports or ledges 24a and 24b. Ledges 24a and 24b also form the respective tops of ramps 26a and 26b that upwardly extend at an angle from the ceiling of recess 18 formed at the junction joining body 4 to neck 10. Ramps 26a and 26b assist in the fitting of the needle hub, as shown in FIG. 5, to neck 10, as will be discussed infra.

At the distal end of neck 10, i.e., the junction where neck 10 meets elongate needle housing 12, there is a thinning of the material for the vacuum tube holder 2. At this weakened junction or joint, designated by the double dotted line 28, the thinning may be effected by a circumferential notching of the material so that an inward circumferential notch 30 is formed at joint 28. Although remaining one piece during shipping and before use, due to the weakened joint 28, when a predetermined or given torque force is applied to needle cover 12 relative to either neck 10 or body 4, the elongate needle cover 12 could readily be separated or removed, at joint or junction 28, from the remainder portion of vacuum tube holder 12.

Given that the vacuum tube holder 2 is molded in one piece, once separated, elongate needle cover 12 could not be reattached to neck 10. As a result, weakened joint 28 provides a tamper evident seal for the vacuum tube holder 2. In other words, if there is any kind of breakage at joint 28, a user such as a phlebotomist will know that the seal has been broken for that particular vacuum tube holder, and that the needle assembly fitted thereto, to be discussed later, may no longer be sterile or fit for use. To enhance a user's ability to separate elongate needle cover 12 from body 4, a number of elongate ribs 32 extending longitudinally along the outer surface of elongate needle cover 12 are provided during the molding process. See FIG. 3a.

As best shown in the bottom view of FIG. 3b, the proximal end of the cylindrical body 4 is supported by a base 34 which is configured in a semi-elliptical shape so as to allow the placement of the vacuum tube holder against the body of a patient at either side 36a or 36b. Sides 36a and 36b prevent the cylindrical body 4 from rotating and thereby falling off the body, for example the arm of the patient. In addition to showing opening 6, FIG. 3b also shows aperture 16 of neck 10. Moreover, the bottom view of FIG. 3b shows the two orifices 20a and 20b formed at neck 10.

FIG. 4 is an enlarged semi-cross sectional view 14 of FIG. 3a.

FIG. 5 is a perspective view of a needle hub assembly 38 that is to be fitted to the vacuum tube holder shown in FIGS. 1-4. With reference also to FIGS. 6 and 7, the needle hub assembly 38 of the instant invention is shown to have a distal section 40 and a proximal section 42. The distal and proximal sections are formed about a double-ended needle 41 having one end 43, which is to be used to prick a patient, extending from the distal end 44 of distal section 40. The other end of the double-ended needle 40, designated 46, extends from the proximal end 48 of proximal section 42. Once properly fitted to vacuum tube holder 2, needle end 43 extends into and is covered by elongate needle cover 12, while needle end 46 extends into cavity 8 of cylindrical body 4. Distal section 40 and proximal section 42 in combination form the needle hub 48 of needle hub assembly 38.

Needle hub 48, at both distal section 40 and proximal section 42, is shown not to be solid, but rather has a number of grooves 50. Grooves 50 are provided in needle hub 48 to possibly lower the cost of manufacturing by eliminating materials that are not needed and also decrease the weight of the needle hub. Distal section 40 of needle hub 48 is dimensioned to have a diameter that fits into the void 52 (FIG. 2) that extends from aperture 16 of neck 10 into the cavity of elongate needle cover 12. Proximal section 42, on the other hand, is dimensioned to fit into the cavity of neck 10 as it is introduced into aperture 16.

Integrally formed at opposite sides, at 180°, of proximal section 42 are catches 54a and 54b. Catches 54a and 54b are assisted by ramps 46a and 46b, when needle hub 48 is press fit to neck 10, after needle hub assembly 38 has been inserted to cavity 8 of body 4. To provide flexibility for catches 54a and 54b so that catches 54a and 54b may move transversely relative to the longitudinal axis of needle hub 48, through slots 56a and 56b are formed in proximal section 48 substantially behind catches 54a and 54b, respectively. A better view of the through slots 56a and 56b may be had with respect to FIG. 10, which is an enlarged view showing the mating of needle hub 48 to neck 10 of the vacuum tube holder. Another view of the through slots 56a and 56b may be had with respect to FIG. 7.

Given that distal section 40 has a smaller diameter than proximal section 42, a ledge 58 is formed circumferentially about needle hub 48 at the intersection of distal section 40 and proximal section 42. Ledge 58 abuts against the bottom of internal shoulder 60 at neck 10, as shown in FIGS. 2 and 4, to prevent distal section 40 from moving further into the cavity of elongate needle cover 12, when needle hub 48 is press fit through aperture 16 into neck 10. Shoulder 60 is designed with sufficient tolerance to allow catches 54a and 54b to be snap fitted to orifices 20a and 20b, respectively, before it abuts ledge 58.

Given the space provided by through slots 56a and 56b, as needle hub 48 is pushed forward into neck 10 via aperture 16, catches 54a and 54b are flexibly compressed by ramps 26a and 26b, until the lowermost portion of those catches move beyond ledges 24a and 24b. At that point, due to their inherent flexibility, catches 54a and 54b would return to their respective original positions with respect to needle hub 48 so that their respective bottom surfaces 60a and 60b rest on and are supported by ledges 24a and 24b. In essence, catches 54a and 54b, acting as one part or portion of a locking mechanism, latch onto orifices 20a and 20b, respectively, which are acting as another part of portion of the locking mechanism, for fixedly retaining needle hub assembly 38 within vacuum tube holder 2. Once thus latched, needle hub 48 is fixedly retained in neck 10 of the vacuum tube holder. To prevent any further forward movement, a base plate 62 integrally forming the proximal end of proximal section 42 is dimensioned to fittingly mate with recess 18 formed at the intersection of neck 10 and body 4. Once mated with recess 18, plate 62 prevents any further forward movement of needle hub 48 toward neck 10.

To enclose needle end 46, which extends into cavity 8 of body 4 of the vacuum tube holder, a barb 64 is integrally formed from the proximal end 48 of proximal section 42. A rubber boot 66 as shown in FIGS. 8a and 8b is fitted over needle end 46, with its upper end 68 being fixedly held to barb 64, as is conventionally known.

With respect to FIGS. 9 and 10, a completely assembled vacuum tube holder assembly is shown to include the one piece molded vacuum tube holder 2, the one piece molded needle hub assembly 38 fitted to and fixedly held within vacuum tube holder 2, and a safety needle housing 72 rotatably mounted about the neck of vacuum tube holder 2.

In particular, needle housing 72 is flexibly or hingedly attached to a collar or ring 74 by way of a living hinge 76. Needle housing 72 has an elongate slot, not shown, that allows it to pivot over and cover needle end 43, while the needle passes through the slot, after elongate needle cover 12 has been removed from vacuum tube holder 2. There are integral hooks 78 provided in housing 72 for fixedly grabbing end needle 43 once housing 72 has been pivoted to a position in substantial alignment along the longitudinal axis of needle 43, or vacuum tube holder 2. Needle protection housing 72 may also be made from polypropylene A more detailed disclosure of a needle protection housing similar to needle protection housing 72 is given in the aforenoted '285 patent, whose disclosure has been incorporated to the instant specification.

The enlarged view of FIG. 10 shows the needle hub assembly having been fittingly mated to vacuum tube holder 2. More specifically, distal section 40 and proximal section 42 of needle hub assembly 38 are shown to have been mated to neck 10 of the vacuum tube holder and fixedly retained thereat. Moreover, collar 74 is shown to be rotatably mounted about neck 10, at protuberance 22, so that collar 74, and therefore housing 72 attached thereto, is rotatable about neck 10 relative to double-ended needle 41. By design, sufficient friction is provided between protuberance 22 and the internal groove of collar 74 so that collar 72 is not freely rotatable. Thus, to rotate housing 72, a torque force has to be applied thereto.

As was mentioned before, to assemble, the one piece needle hub assembly 38, which may also be made from polypropylene, is first inserted into cavity 8 through opening 6 at the proximal end of the cylindrical body 4 of vacuum tube holder 2. Needle hub 48 of needle hub assembly 38 is then press fit to neck 10 of vacuum tube holder 2 until catches 54a and 54b latch onto orifices 20a and 20b, respectively, formed at the opposite sides of neck 10. Once catches 54a and 54b extend out into orifices 20a and 20b, respectively, their respective bottom surfaces 60a and 60b would act against ledges 24a and 24b of orifices 20a and 20b, respectively. As a result, the needle hub 48 could no longer be moved in a backwards direction, i.e., toward opening 6 of body 4. The ledge 58 formed at the intersection of distal section 40 and proximal section 42 of needle hub 48 and plate 62 formed at the base of proximal section 42 prevent further forward movement of the needle hub. Needle protection housing 72, by way of collar 74 connected thereto, is rotatably mounted about neck 10 of the vacuum tube holder. More specifically, the internal groove of collar 74 is rotatably mated to the protuberance that circumferentially forms about the outer wall surface of neck 10.

To use, a user applies a predetermined torque force to elongate needle cover 12 relative to neck 10 or body 4 to separate the needle cover from neck 10 of the vacuum tube holder, at weakened joint 30. After use and possibly after a vacuum tube inserted into cavity 8 of body 4 which is pierced by end needle 46 has been removed, the contaminated end needle 43 is fixedly held within needle protection housing 72, by the user pivotally moving needle protection housing 72 towards needle end 42 until needle end 43 is grasped by hooks 78 integral in housing 72.

By producing a one piece molded vacuum tub holder, and by press fitting a one piece molded needle hub assembly to the vacuum tube holder, the processing steps for manufacturing the instant inventive vacuum tube holder assembly are made simpler and more economical. If desired, opening 6 of the vacuum tube holder may be sealed with a material that allows sterilization gas to pass through so that the completely assembled device such as that shown in FIG. 9 may be readily sterilized and shipped, without any need for separate needle cover sheaths and tamper evident warning labels or seals.

With reference to FIGS. 11a-11d and FIGS. 12-14, embodiments of a finger grasp mechanism such as for example a wing nut which may be added to needle cover 12 of the inventive vacuum tube holder are shown. The first wing nut embodiment is shown in FIGS. 11a-11d while the second wing nut embodiment is illustrated in FIGS. 12-14.

The addition of a finger grasp mechanism such as a wing nut or other means that amplifies the torque force applied by a user to the needle cover of the inventive vacuum tube holder solves the following dilemma. Without the wing nut structure, circumferential notch 30 of the inventive vacuum tube holder has to be designed to have a thickness that breaks when a torque force of approximately 30 ounce inches is applied to needle cover 12, relative to either neck 10 or body 4. Most, if not all users, could readily apply such torque force of approximately 30 ounce inches to separate needle cover 12 from body 4. Yet during shipping and handling, it was found that needle cover 12 could be inadvertently broken off or separated from neck 10. It was also found that a thickness for the circumferential notch 30 that allows shipping and handling without inadvertent separation of the needle cover from the vacuum tube holder is approximately 60 ounce inches. Yet by increasing the thickness of circumferential notch 30 also means that a user has to apply a greater torque force to twist needle cover 12 off neck 10. Depending on their strengths, some people may find the twisting off of needle cover 12 from the vacuum tube holder having a thickened notch to be doable while others would have a difficult time.

The addition of a wing nut to the needle cover of the vacuum tube holder having a thickened notch achieves the happy medium of preventing inadvertent separation of the needle cover from the body of the vacuum tube holder during transit and handling, and yet at the same time allowing most if not all of the users to readily remove the needle cover from the body of the vacuum tube holder by applying an intentional torque force of no greater, or not much greater, than that before the neck of the vacuum tube holder was thickened. This is due to the finding that, with the coupling of the wingnut to the needle cover, a torque force of approximately 30 ounce inches applied by the user to the wings of the wingnut would generate a torque force of greater than approximately 60 ounce inches to the needle cover, relative to the body of the vacuum tube holder. Thus, a vacuum tube holder having a thickened notch 30 that could withstand a torque force of approximately 60 ounce inches, and therefore inadvertent breakage, could be manufactured.

Figure 11A:
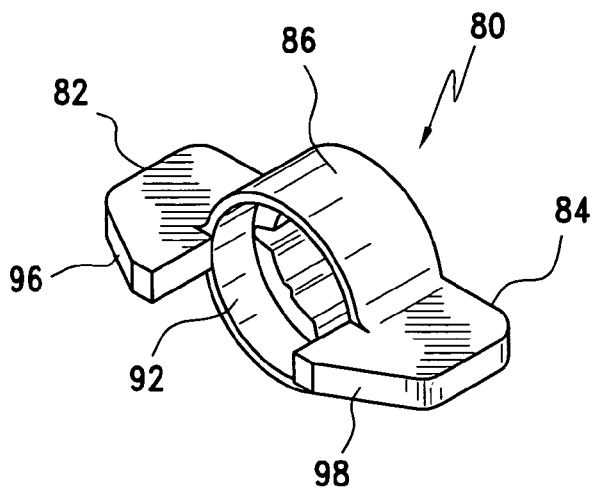
FIGS. 11a-11d are views of a first embodiment of a finger grasp mechanism in the form of a wing nut to be added to the vacuum tube holder assembly.
Figure 11B:
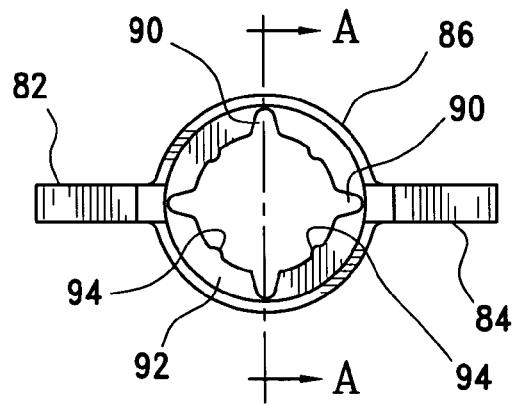
Figure 11C:
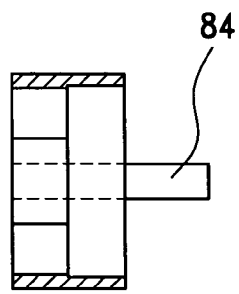
Figure 11D:
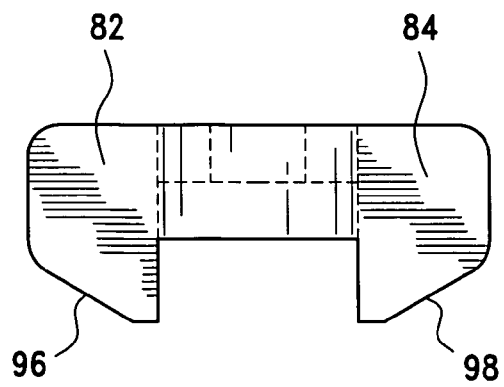

The first embodiment of the finger grasp wing nut, designated 80, is shown in FIGS. 11a-11d. FIG. 11a shows a prospective view of wing nut 80, which has two wings 82 and 84 extending away from its outer wall 86. As best shown in FIG. 11b, wing nut 80 has a bore 88, which is shaped to have a number of slots or channels 90 formed at its inner wall 92. The top view of wing nut 80 also shows that there are a number of extensions 94 extending inwardly toward the center of bore 99 from inner wall 92. Each of wings 82 and 84 has a leg portion, designated 96 and 98, respectively.

A second embodiment of the wing nut that enables a user to grasp and twist, per her fingers, is illustrated in FIGS. 12-14. The components of the wing nut for the second embodiment that are the same as the first embodiment are labeled the same. As shown, the second embodiment of the wing nut is the same as the first embodiment except for two additional legs 100 and 102 that extend downwards from outer wall 86 of the wing nut. Note that each of extension legs 100 and 102 has a bottom surface, designated 104 and 106, respectively. In addition, each of legs 96 and 98 of corresponding wings 82 and 84 has a bottom surface 106 and 108, respectively. Note that for both of the embodiments of the wing nut, the wings 82 and 84 provide a user means by which to grasp the wing nut with her fingers for effecting a twisting motion, i.e., applying a torque thereagainst.

Figure 15:
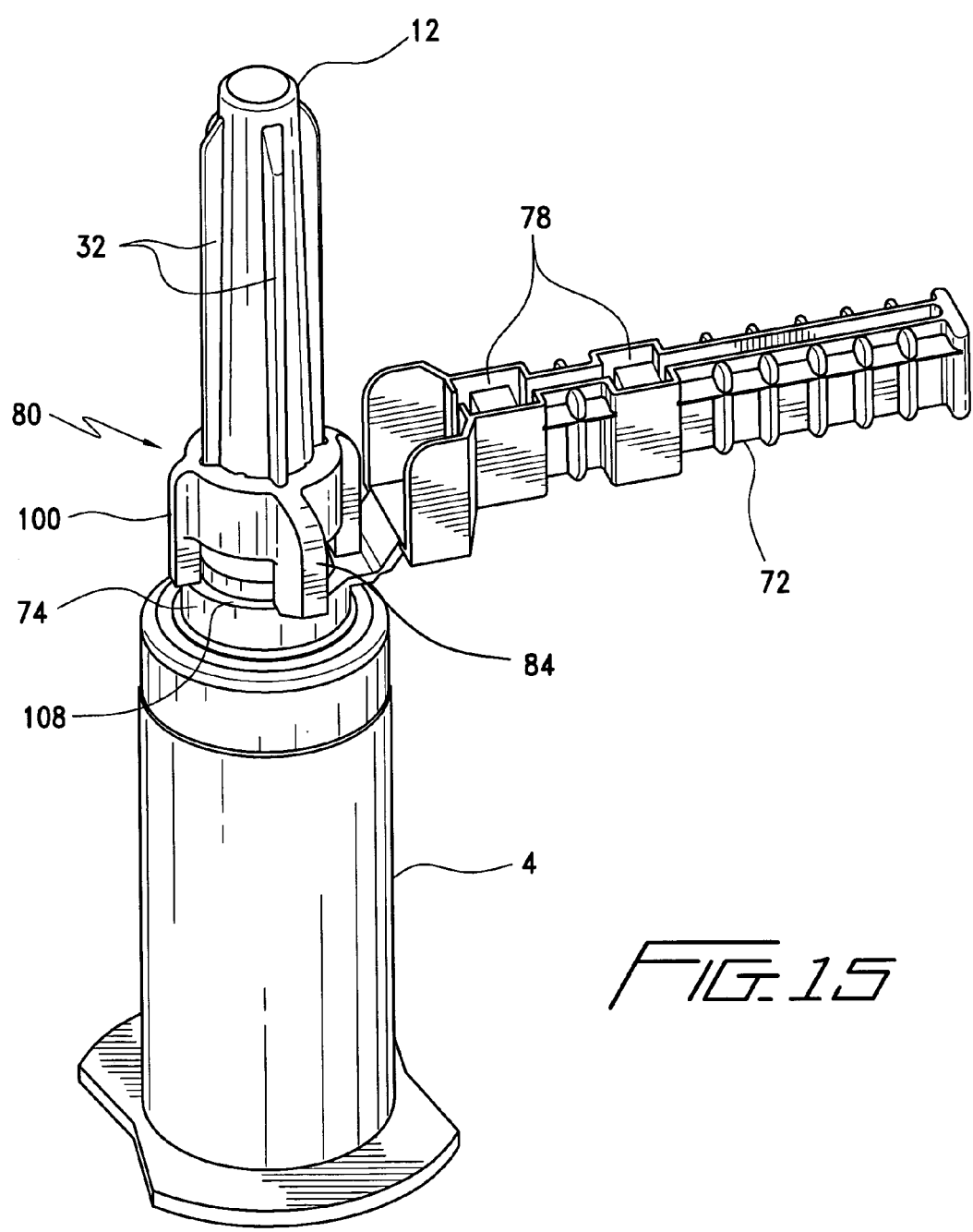
FIG. 15 is a perspective view of the inventive vacuum tube holder assembly that has added thereto the wing nut embodiment as shown in FIGS. 12-14.
Figure 16:
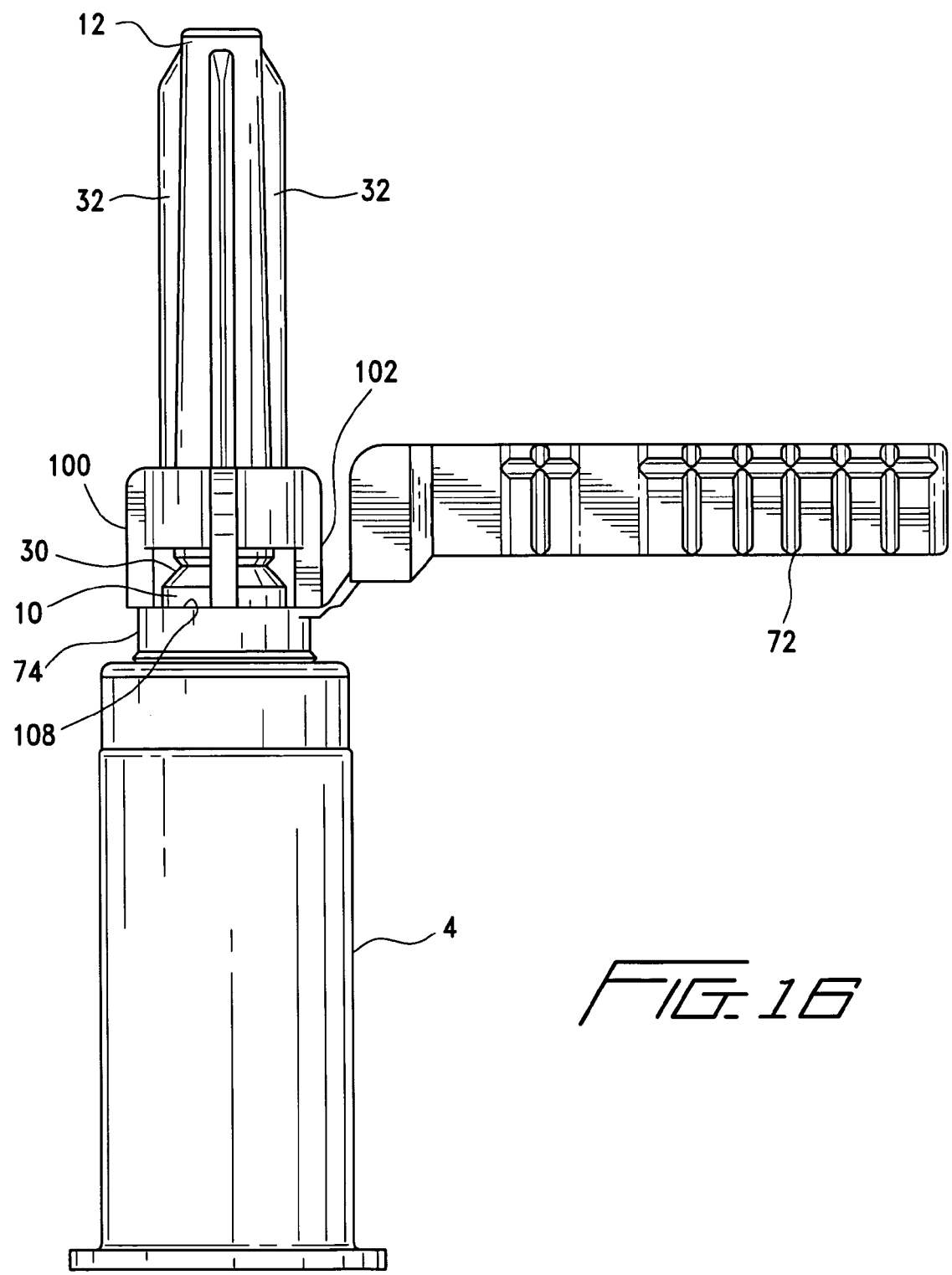
FIG. 16 is a side view of the FIG. 15 vacuum tube holder assembly.

With reference to FIGS. 15-17, wing nut 80, as represented by the second embodiment of FIGS. 12-14, is shown to be coupled to needle cover 12 of vacuum tube holder 2. As shown, wing nut 80 has been slidably fitted to needle cover 12 by having each of its internal slots 90 ride on a corresponding rib 32 that extends longitudinally substantially along the length of needle cover 12. Although wing nut 80 may be provided at any location along the length of needle cover 12, for the embodiment shown in FIG. 15 and the instant discussion, wing nut 80 is shown to be positioned at the proximal portion of needle cover 12. Once positioned at the desired location along needle cover 12, bonding, by epoxy or electric welding, may be effected between the outer wall of needle cover 12 and the inner wall 92 of wing nut 80. The bonding of wing nut 80 to needle cover 12 may in particular be effected between the plurality of extensions 94 at the inside wall 92 of wing nut 80 and the outer wall of needle cover 12.

To provide stability, top surface 108 of rotatable collar 74 provides a rest stop for the downward movement of wing nut 80, by acting against the bottom surfaces of leg extensions 100, 102 and legs 96 and 98 of wings 82 and 84, respectively. Given the characteristics of the materials, namely polypropylene from which the needle cover and the wing nut are made of, sufficient elasticity is provided to enable the wing nut to be slide fitted to the desired proximal end of needle cover 12, and be held thereat by friction, once the force for pushing the wing nut along the length of the needle cover is removed. Accordingly, for the instant invention, it should be noted that it may not be necessary that wing nut 30 be bonded to needle cover 12, when even without such bonding, wing nut 30 is snugly coupled to needle cover 12. Once needle cover 12 is removed from neck 10, wing nut 30 is removed therealong and is discarded along with needle cover 12.

By thus fixedly coupling wing nut 80 to needle cover 12, the circumferential groove 30 may be thickened so that the vacuum tube holder assembly, as shown in FIGS. 15-17, may be shipped and handled as a single unit without needle cover 12 being inadvertently separated from neck 10 of body 4. Indeed, the thickness of circumferential notch 30 may be designed to be such that it affords integrity during shipment and yet at the same time enables a user to readily remove needle cover 12 from neck 10 by applying a twist motion to wing nut 80. Empirical studies show that the thickness of circumferential notch 30 may be designed to withstand a torque force of approximately 60 ounce inches, which is approximately double the torque that a user could comfortably exert for removing a needle cover 12 for a thickened notched vacuum tube holder that has not been fitted with a wing nut 30. Thus, with the embodiment of the vacuum tube holder assembly as shown in FIGS. 15-17, when a user applies a twisting force to the wing nut, due to the configuration of the wing nut, a torque force greater than approximately 60 ounce inches is applied to needle cover 12 to thereby readily separate the same from neck 10 of the vacuum tube holder.

Although wing nut 80 is shown to be slidably fitted to needle cover 12, it should be appreciate that wing nut 80 may in fact be integral to needle cover 12, as the manufacturing process may be such that the inventive vacuum tube holder may be molded to include the wing nut as part of its needle cover. Indeed, when so integrated, the ring portion of the wing nut is no longer needed. Thus, for this invention, it is assumed that a wing nut may define only wings coupled to the needle cover. Further, other finger grasp means that could amplify the torque force applied by the user may also be coupled to the needle cover.

By having the wings extending from the outer wall of the main body, or the ring of the wing nut, a user can actually remove needle cover 12 from neck 10 of the vacuum tube holder in a one-handed operation, for example by holding the body with the digits and palm of her hand while at the same time pushing her thumb against one of the wings of the wing nut. The adding of a wing nut to the vacuum tube holder assembly therefore allows intentional, yet-easy, removal of the needle cover from the vacuum tube holder assembly.

The invention claimed is:

1. Apparatus, comprising:
    a one piece cylindrical body having an opening at one end through which a fluid storage tube is insertable and a neck that has an elongate needle cover integrally extending therefrom, said cover being integrally joined to said neck at a weakened joint, finger grasp means coupled to said cover at a desired location along the length of said cover to amplify the torque force applied by a user to said cover when the user applies a predetermined torque to said finger grasp means to rotate said cover relative to said body to separate said cover from said neck at said weakened joint, said predetermined torque if applied anywhere along the length of said cover whereto said finger grasp means is not coupled would fail to separate said cover from said neck, said neck having an aperture dimensioned to accept a needle hub;
    wherein said needle hub is a part of a needle hub assembly comprising a base having a double ended needle extending therethrough, said needle hub including a proximal section having at least one catch and a distal section that is dimensioned to extend from a distal end of said neck when said needle hub is fully inserted to said aperture, said catch snappingly latching to a side orifice at said neck when said assembly is fully inserted to said aperture.

2. A needle holder assembly, comprising:
    a cylindrical body having
        an opening at one end through which a fluid storage tube is insertable,
        a neck having one lock mechanism formed transverse to a side thereof,
        an elongate cover having a longitudinal length integrally extending from said neck and joined to said neck at a weakened joint, and
        finger grasp means fixedly mounted to a desired location along the length of said elongate cover, said finger grasp means having at least one wing extending away from said elongate cover;
    a needle hub assembly having
        a proximal section and a distal section,
        a double ended needle extending through said distal and proximal sections, and
        an other lock mechanism formed at the outer surface of said proximal section;
    wherein said needle hub assembly is fixedly fitted within said body with at least said proximal section fitted within said neck and said one and other lock mechanisms in a locking relationship; and
    wherein said cover is separable from said neck at said weakened joint when a predetermined torque is applied to said wing relative to either said body or said neck;
    wherein said one lock mechanism comprises a pair of orifices formed transversely at opposite sides of said neck and wherein said other lock mechanism comprises a pair of catches formed at opposite sides of the outer surface of said proximal section, each of said catches latching onto a corresponding one of said orifices when said needle hub assembly is inserted to said body and said proximal section is press fitted to said neck; and
    wherein said neck has an aperture dimensioned to accept said proximal section and at least a portion of said distal section of said needle hub assembly.

3. A one piece molded needle holder, comprising: a cylindrical body having a cavity and an opening at one end through which a fluid storage tube is insertable to said cavity, said body ending with a neck having at least one orifice formed transverse to a side thereof, said neck having an aperture smaller in dimension than said cavity, a needle cover having a longitudinal length integrally joined to and extending from the end of said neck away from said body, a notch formed circumferentially about the junction where said neck is joined to said cover to effect a weakened joint, finger grasp means coupled to a desired location along the length of said needle cover to enable a user to twist off said needle cover from said neck by applying a predetermined torque thereto.

4. Needle holder of claim 3, wherein said neck comprises a pair of orifices formed at opposite sides thereof, said needle holder further comprising a collar having a housing pivotably attached thereto rotatably mounted about said neck, said housing pivotable to a position in alignment along the longitudinal axis of said holder for covering a needle extending from a needle assembly mated to said neck, a hook integral in said housing fixedly holding said needle once said housing is pivoted to said alignment position.

5. Needle holder of claim 3, wherein said finger grasp means comprises a wing nut, and said needle cover is separable from said body when said predetermined torque applied to said wing nut is less than approximately 60 ounce inches; and wherein said needle cover, once separated from said neck at said joint, is not attachable back to said neck.

6. A one piece molded needle hub assembly to be used with the molded needle holder of claim 3, comprising: a proximal section and a distal section, said proximal section dimensioned to fit to the aperture of the neck of said holder, a double ended needle extending through said distal and proximal sections, a pair of catches formed at opposite sides of the outer circumference of said proximal section, and a through slot formed in said proximal section behind each of said catches to enable flexible movements of said catch transversely to said proximal section.

\* \* \* \* \*